United States Patent
Kinney et al.

(10) Patent No.: US 9,079,896 B2
(45) Date of Patent: Jul. 14, 2015

(54) UROTENSIN II RECEPTOR ANTAGONISTS

(75) Inventors: William A. Kinney, Newtown, PA (US); Diane K. Luci, Horsham, PA (US); Bruce E. Maryanoff, Forest Grove, PA (US); Shyamali Ghosh, Norristown, PA (US); Edward C. Lawson, Pipersville, PA (US)

(73) Assignee: Janssen Pharmaceutica NV (BE)

( * ) Notice: Subject to any disclaimer, the term of this patent is extended or adjusted under 35 U.S.C. 154(b) by 1166 days.

(21) Appl. No.: 12/533,257

(22) Filed: Jul. 31, 2009

(65) Prior Publication Data

US 2010/0029616 A1 Feb. 4, 2010

Related U.S. Application Data

(60) Provisional application No. 61/137,634, filed on Aug. 2, 2008.

(51) Int. Cl.
C07D 487/12 (2006.01)
C07D 471/04 (2006.01)
C07D 487/04 (2006.01)

(52) U.S. Cl.
CPC .......... C07D 471/04 (2013.01); C07D 487/04 (2013.01)

(58) Field of Classification Search
None
See application file for complete search history.

(56) References Cited

U.S. PATENT DOCUMENTS

| | | | |
|---|---|---|---|
| 3,629,266 A | 12/1971 | Havera | |
| 6,011,050 A | 1/2000 | Muller et al. | |
| 6,544,992 B1 | 4/2003 | Dhanak et al. | |
| 6,583,144 B2 | 6/2003 | Ohkura et al. | |
| 6,884,887 B1 | 4/2005 | Riermeier et al. | |
| 6,911,464 B2 | 6/2005 | Man et al. | |
| 7,043,052 B2 | 5/2006 | Rhoads | |
| 7,307,075 B2 | 12/2007 | Skjacrback et al. | |
| 7,790,715 B2 | 9/2010 | Herold et al. | |
| 7,915,260 B2 | 3/2011 | Maryanoff et al. | |
| 7,968,570 B2 | 6/2011 | Clayton et al. | |
| 8,008,299 B2 | 8/2011 | Kinney et al. | |
| 8,193,191 B2 | 6/2012 | Maryanoff et al. | |
| 2001/0049371 A1 | 12/2001 | Muller et al. | |
| 2004/2299871 | 11/2004 | Cesure et al. | |
| 2004/0259873 A1 | 12/2004 | Man et al. | |
| 2004/0267051 A1 | 12/2004 | Boerner et al. | |
| 2005/0143393 A1 | 6/2005 | Dean et al. | |
| 2005/0203090 A1 | 9/2005 | Man et al. | |
| 2005/0239867 A1 | 10/2005 | Zeldis | |
| 2005/0282819 A1 | 12/2005 | Graham | |
| 2007/0027163 A1 | 2/2007 | Bissantz et al. | |
| 2008/0039454 A1 | 2/2008 | Ghosh et al. | |

FOREIGN PATENT DOCUMENTS

| | | |
|---|---|---|
| WO | 98/52919 A1 | 11/1998 |
| WO | 01/05741 | 1/2001 |
| WO | 02/47687 | 6/2002 |
| WO | 03/014061 | 2/2003 |
| WO | 03/091248 | 11/2003 |
| WO | 03/104216 | 12/2003 |
| WO | 2004/024702 | 3/2004 |
| WO | 2004/078114 | 9/2004 |
| WO | 2004/080422 | 9/2004 |
| WO | 2004/080423 | 9/2004 |
| WO | 2005/034873 | 4/2005 |
| WO | 2005/034873 A2 | 4/2005 |
| WO | 2005/034873 A3 | 4/2005 |
| WO | 2005/061457 | 7/2005 |
| WO | 2005/072226 | 8/2005 |
| WO | 2005/072226 A2 | 8/2005 |
| WO | 2005/072226 A3 | 8/2005 |
| WO | 2006/020879 | 2/2006 |
| WO | 2007/008541 | 1/2007 |
| WO | 2008/016534 | 2/2008 |
| WO | 2007/081995 | 7/2008 |
| WO | 2008/153902 | 12/2008 |

OTHER PUBLICATIONS

Jantzen and Robinson. Modern Pharmaceutics, 1996, 596.*
"Metabolite", http://www.encyclopedia.com/doc/1E1-metabolit.html, 2007.*
MERTENS. Journal of Medicinal Chemistry, 1993, 36(17), 2526-2535.*
Pearson, D., et al., "Urotensin II: A Somatostatin-like peptide in the caudal neurosecretory system of fishes", *Proc. Natl. Acad. Sci.*, 1908, pp. 5021-5024, vol. 77, No. 8.
Ames, RS., et al., "Human urotensin-II is a potent vasoconstrictor and agonist for orphan receptor GPR14", *Nature*, 1999, pp. 282-286, vol. 401.
Tal, M., et al., "A Novel Putattive Neuropeptide Receptor Expressed in Neural Tissue Including Sensory Epithelia", *Biochem. Biophys. Res. Comm.*, 1995, pp. 752-759, vol. 209, No. 2.
Marchese, A., et al., "Cloning and Chromosomal Mapping of Three Novel Genes, GPR9, GPR10, and GPR14, Encoding Receptors Related to Interleukin 8, Neuropeptide Y, and Somatostatin Receptors", *Genomic*, 1995, pp. 335-344, vol. 29.

(Continued)

*Primary Examiner* — Noble Jarrell
(74) *Attorney, Agent, or Firm* — Yuriy P. Stercho

(57) ABSTRACT

The present invention is directed to compounds of formula (I)

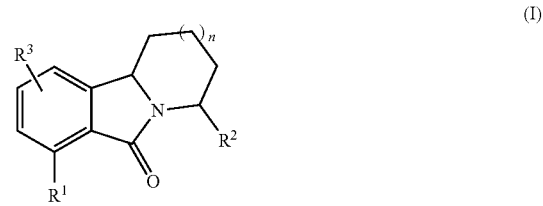

and pharmaceutically acceptable salts, esters and prodrugs thereof, pharmaceutical compositions containing compounds of formula (I) and the use of said compounds and compositions as urotensin II receptor antagonists.

6 Claims, No Drawings

(56) References Cited

OTHER PUBLICATIONS

Conlon, J.M., et al., "Distribution and Molecular Forms of Urotensin II and Its Role in Cardiovascular Regulation in Vertebrates", *J. of Exp. Zool.*, 1996, pp. 226-238, vol. 275.
Bohm, F., et al., "Urotensin II evokes potent vasoconstriction in humans in vivo", *Br. J. of Pharmacol.*, 2002, pp. 25-27, vol. 135.
Douglas, S.A., et a., "Human Urotensin-II, the Most Potent Mammalian Vasoconstrictor Identified to Date, as a Therapeutic Target for the Management of Cardiovascular Disease", *Trends Cardiovasc. Med.*, 2000, pp. 229-237, vol. 10.
Zou, Y., et al., "Urotensin II induces hypertrophic responses in cultured cardiomyocytes from neuronal rats", *FEBS Lett.*, 2001, pp. 57-60, vol. 508.
Watanabe, T., et al., "Synergistsic Effect of Urotensin II with Mildly Oxidized LDL on DNA Synthesis in Vascular Smooth Muscle Cells", *Circulation*, 2001, pp. 16-18, vol. 104.
Lim, M., et al., "Differential Effect of Urotensin II on Vascular one in Normal Subjects and Patients with Chronic Heart Failure", *Circulation*, 2004, pp. 1212-1214, vol. 109.
Bousette, N., et al., "Increased expression of urotensin II and its cognate receptor GPR14 in atherosclerotic lesions of the human aorta", *Artherosclerosis*, 2004, pp. 117-123, vol. 176.
Totsune, K., et al., "Role of Urotensin II in patients on dialysis", *Lancet*, 2001, pp. 810-811, vol. 358.
Silvestre, R.A., et al., "Inhibition of Insulin Release by Urotensin II—A Study on the Perfused Rat Pancreas", *Horm. Metab. Res.*, 2001, pp. 379-381, vol. 33.
Totsune, K., et al., "Increased plasma urotensin II levels in patients with diabetes mellitus", *Clin. Sci.*, 2003, pp. 1-5, vol. 104.
Garlton, J., et al., "Central effects of urotensin-II following ICV administration in rats", *Psychopharmacology*, 2001, pp. 426-433, vol. 155.
Garlton, J.E., et al., "Urotensin-II, a neuropeptide ligand for GPR14, induce c-*fos* in the rat brain", *Eur. J. of Pharmacol.*, 2004, pp. 95-98, vol. 493.
Matsumoto, Y., et al., "Intracerebroventricular administration of urotensin II promotes anxiogenic-like behavior in rodents", *Neurosci. Lett.*, 2004, pp. 99-102, vol. 358.
Bousette, N., et al., *American Heart Association—Scientific Sessions*, 2005 (Abstract Only).
Hall, A. Am Chem Soc., 1957, 79, 5444-5447.
Kinney, W.A., et al., "Structure-Function Analysis of Urotensin II and Its Use in the Construction of a Ligand-Receptor Working Model", *Agnew. Chem., Intl. Ed.*, 2002, pp. 2940-2944, vol. 41.
Qi, J-S., et al., "Characterization of function urotensin II receptors in human skeletal muscle myoblasts: comparison with angiotensin II receptors", *Peptides*, 2005, pp. 683-690, vol. 26.
Ong, et al., "Haplotypes in The Urotensin II Gene and Urotensin II receptor gene are Associated with Insulin Resistance and Impaired Glucose Tolerance", Peptides, 2006, 27(7), 1659-1667.
Clozel, et. al., J. Pharmacol. Exp. Ther. 2006, 316 (3), 1115-1121.
Bousette, et al., "Urotensin-II blockage with SB-611812 Attenuates Cardiac Dysfunction in a Rat Model of Coronary Artery Ligation", Journal of Molecular and Cellular Cadiology 2006, vol. 41 pp. 285-295.
Eastwood, "A Versatile synthesis of 4-aryl Tetrahydropyridines Via Palladium Mediated Suzuki Cross-Coupling With Cyclic Vinyl Boronates", Tetrahedron, Lett., 2000, 41, pp. 3705-3708.
Ghosh, et al., "Convenient Preparation of Aryl-Substituted Nortopanes by Suzuki-Miyaura Methodology" Canadian Journal of Chemistry 2006. 84, 555-560.
Beak, et al., "A-Lithioamine Synthetic equivalents: Syntheses of Diastereoisomers from Boc Derivatives of Cyclic Amines", J. Org. Chem. 1993, 58, pp. 1109-1117.
Gillaspy, et al., "A Simple Method for the Formation of Cycolpropylamines: The First Synthesis of Tricyclopropylamine," Tetrahedrpm: Letters. 1995, pp. 7399-7402, vol. 36.
Vippagunta, et al., "Crystalline Solids", Advanced Drug delivery reviews, pp. 3-26, vol. 48 2001.
Jian, et al., "Non-Peptidic Urotensin-II Receptor Modulators", Expert Opinion on Therapeutic Patents, Apr. 2006, pp. 467-479, vol. 16, No. 4.
Bank and Rhodes, Modern Pharmaceutics, Third Edition, p. 596, 1996.
EP Search Report, PCT/US2007000644, dated Jun. 7, 2010.
ISR, PCTUS07/00644, dated Dec. 9, 2007.
ISR, PCT/US08/07076, dated Aug. 20, 2008.
JP Rejection, appl. 2009-522801, dated Oct. 11, 2012.
EP Search Report, 09 791 047.5 2101, Dated May 27, 2011.
ISR, PCT/US2009/052403. Dated Nov. 31, 2009.

\* cited by examiner

UROTENSIN II RECEPTOR ANTAGONISTS

RELATED APPLICATION

This application claims the benefit of U.S. Provisional Application No. 61/137,634, filed Aug. 2, 2008, which is incorporated herein by reference in its entirety.

FIELD OF THE INVENTION

The present invention relates to novel tricyclic compounds, methods for preparing said compounds, compositions containing said compounds and the use of said compounds for the treatment of urotensin-II mediated disorders. More particularly, the compounds of the present invention are urotensin-II receptor antagonists useful for treating urotensin-II mediated disorders.

BACKGROUND OF THE INVENTION

Urotensin-II (U-II) is a cysteine-linked cyclic peptide, which exerts potent effects on the cardiovascular, renal, pancreatic, and central nervous systems. Originally, this substance was isolated from the urophysis (a caudal neurosecretory organ) of the goby fish (*Gillichthys mirabilis*) as a 12-mer, AGTAD-cyclo(CFWKYC)-V (D. Pearson. J. E. Shively, B. R. Clark, I. I. Geschwind, M. Barkley, R. S, Nishioka, H. A. Bern, *Proc. Natl. Acad. Sci. USA* 1980, 77, 5021-5024), but it has now been identified in all classes of vertebrates. The composition of U-II ranges from 11 amino acids in humans to 14 amino acids in mice, always with a conserved cysteine-linked macrocycle, CFWKYC. Recently, the U-II receptor was identified (R. S. Ames, H. M. Sarau, J. K. Chambers, R. N. Willette, N. V. Aiyar, A. M. Romanic, C. S. Louden, J. J. Foley, C. F. Sauermelch, R. W. Coatney, Z. Ao, J. Disa, S. D. Holmes, J. M. Stadel, J. D. Martin, W.-S. Liu, G. I. Glover, S. Wilson, D. E. McNulty, C. E. Ellis, N. A. Elshourbagy, U. Shabon, J. J. Trill, D. W. P. Hay, E. H. Ohlstein, D. J. Bergsma, S. A. Douglas, *Nature* (London) 1999, 401, 282-286) as a G-protein-coupled receptor (GPCR) previously known as the GPR14 orphan receptor, (M. Tal, D. A. Ammar, M. Karpuj, V. Krizhanovsky, M. Naim, D. A. Thompson, *Biochem. Biophys. Res. Commun.* 1995, 209, 752-759; and A. Marchese, M. Heiber, T. Nguyen, H. H. Q. Heng, V. R. Saldivia, R. Cheng, P. M. Murphy, L.-C. Tsui, X. Shi, P. Gregor, S. R. George, B. F. O'Dowd, J. M. Docherty, *Genomics* 1995, 29, 335-344) which is expressed predominantly in cardiovascular tissues.

Goby U-II possesses powerful vasoconstrictor activity in fish, mammals, and humans (J. M. Conlon, K. Yano, D. Waugh, N. Hazon, *J. Exp. Zool.* 1996, 275, 226-238; F. Böhm, J. Pernow, *Br. J. Pharmacol.* 2002, 135, 25-27). Moreover, it appears to be the most potent vasoconstrictor known, (S. A. Douglas, E. H. Ohlstein, *Trends Cardiovasc. Med.* 2000, 10, 229-237), causing concentration-dependent contraction of isolated arterial rings of rats and humans with an $EC_{50}$ value of less than 1 nM, which is ca. ten times more potent than endothelin-1. Recently, Kikkawa, H. and Kushida, H. in International Publication WO 2005/072226 disclosed the use of urotensin-II antagonists for the prevention and/or treatment of inflammatory bowel diseases including, but not limited to, Crohn's disease, ulcerative colitis, and inflammatory colitis caused by bacteria, ischemia, radiation, drugs, or chemical substances.

Relative to the role of U-II in chronic vascular disease, this peptide was reported to induce hypertrophy in cardiomyocytes (Y. Zou, R. Nagai, T. Yamazaki, *FEBS Letters* 2001, 508, 57-60) and the proliferation of smooth muscle cells (T. Watanabe, R. Pakala, T. Katagiri, C. R. Benedict, *Circulation* 2001, 104, 16-18), which suggests an involvement in heart failure and atherosclerosis. In addition, U-II has been shown to increase peripheral vascular tone, a characteristic of chronic heart failure (M. Lim, S. Honisett, C. D. Sparkes, P. Kornesaroff, A. Kompa, H. Krum, *Circulation* 2004, 109, 1212-1214). Recent results have shown increased U-II receptor levels observed in the atherosclerotic lesions of the human aorta (N. Bousette, L. Patel, S. A. Douglas, E. H. Ohlstein, A. Giaid, *Atherosclerosis* 2004, 176, 117-123).

Relative to healthy individuals, the expression of U-II-like immunoreactivity was 2-fold higher in the plasma of patients with renal dysfunction who were not on dialysis, and 3-fold higher in those on haemodialysis (K. Totsune, K. Takahashi, Z. Arihara, M. Sone, F. Satoh, S. Ito, Y. Kimura, H. Sasano, O. Murakami, *Lancet* 2001, 358, 810-811). Recently, Kinoshita, M. and Kushida, H. in International Publication WO 2005/034873 disclosed the use of urotensin-II antagonists for reducing nephrotoxicity and diarrhea caused by anti-neoplastic agents.

U-II has been described as a potential mediator in diabetes. For instance, U-II was shown to inhibit the release of insulin in the perfused rat pancreas in response to increasing glucose levels (R. A. Silvestre, J. Rodriguez-Gallardo, E. M. Egido, J. Marco, *Horm. Metab. Res.* 2001, 33, 379-381). Elevated U-II levels were seen in patients with diabetis mellitus (K. Totsune, K. Takahashi, Z. Arihara, M. Sone, S. Ito, O. Murakami, *Clin. Sci.* 2003, 104, 1-5) even without renal failure.

A U-II antagonist may be useful for the treatment of pain, neurological and psychiatric conditions, migraine, neuromuscular deficit, and cardiovascular disorders. ICV (intracerebroventricular) administration of U-II increases rearing, grooming, and motor activity suggesting a CNS stimulatory activity (J. Gartlon, F. Parker, D. C. Harrison, S. A. Douglas, T. E. Ashmeade, G. J. Riley, Z. A. Hughes, S. G. Taylor, R. P. Munton, J. J. Hagan, J. A. Hunter, D. N. C. Jones, *Psychopharmacology* 2001, 155, 426-433). U-II increases Fos expression in the cingulate cortex and periaqueductal grey brain regions important in cognitive, emotional, and motor responses; the perceptions of pain; and panic responses (J. E. Gartlon, T. Ashmeade, M. Duxon, J. J. Hagan, D. N. C. Jones, *Eur. J. of Pharmacol.* 2004, 493, 95-98). U-II induces anxiogenic-like responses in rodents in the elevated plus maze and hole-board tests (Y. Matsumoto, M. Abe, T. Watanabe, Y. Adachi, T. Yano, H. Takahashi, T. Sugo, M. Mori, C. Kitada, T. Kurokawa, M. Fujino, *Neuroscience Letters* 2004, 358, 99-102).

U.S. Pat. No. 6,911,464 and Application Publications US2004/0259873 and US2005/0203090 (corresponding to Man, H-W. and Muller, G. W. International Publication WO/2004080422) disclose N-alkyl-hydroxamic acid-isoindolyl compounds for treatment or prevention of various diseases and disorders mediated by PDE4 inhibition, associated with abnormal TNF-alpha levels, and/or mediated by MMP inhibition.

U.S. Pat. No. 7,043,052 and Application Publications US2004/0259873 and US2005/0203090 (corresponding to Man, H-W., Muller, G. W., and Zhang, W. International Publication WO2004/080423) disclose 7-amido-isoindolyl compounds for the treatment, prevention or management of various diseases and disorders, including but not limited to cancer, inflammatory bowel disease and myelodysplastic syndrome.

Kawasaki, H., Shinagawa, Y., and Mimura, T. in International Publication WO98/52919 disclose phthalamide derivatives and an antiallergic agent containing the same, having selective IgE and IL-5 production inhibitory activities.

United States Patent Application Publication US2004/0267051 (corresponding to International Publication WO2003/014061) describes a method for the production of amines by reductive amination of carbonyl compounds under transfer-hydrogenation conditions.

U.S. Pat. No. 6,884,887 (corresponding to PCT Publication WO2001/005741) describes a method for producing amines by homogeneously catalyzed reductive amination of carbonyl compounds.

Accordingly, it is an object of the present invention to provide compounds that are urotensin-II antagonists useful for treating urotensin-II mediated disorders. It is another object of the invention to provide a process for preparing compounds, compositions, intermediates and derivatives thereof. It is a further object of the invention to provide methods for treating urotensin-II mediated disorders including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

SUMMARY OF THE INVENTION

The present invention is directed to a compound of Formula (I):

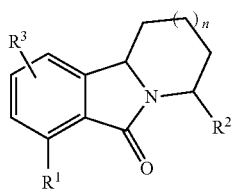

(I)

wherein $R^1$ is selected from the group consisting of hydrogen, halogen, cyano, $C_{1-3}$alkyl, $C_{1-3}$alkoxy and $NR^A R^B$; wherein $R^A$ and $R^B$ are each independently selected from the group consisting of hydrogen and $C_{1-4}$alkyl;

n is an integer from 0 to 3; (preferably n is an integer from 1 to 2)

$R^2$ is selected from the group consisting of phenyl and 5 to 6 membered heteroaryl; wherein the phenyl or 5 to 6 membered heteroaryl is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, $(C_{1-4}$alkyl)amino, di$(C_{1-4}$alkyl)amino and —C(O)O—$C_{1-4}$alkyl;

$R^3$ is bound at the three or the four position, and is $NR^C R^D$; wherein $R^C$ and $R^D$ are each independently selected from the group consisting of hydrogen and $C_{1-4}$alkyl;

alternatively, $R^C$ and $R^D$ are taken together with the nitrogen atom to which they are bound to form a saturated ring structure selected from the group consisting of piperidinyl, piperazinyl and pyrrolidinyl;

wherein the saturated ring structure is optionally substituted with one or more substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, $(C_{1-4}$alkyl)amino, di$(C_{1-4}$alkyl)amino and —C(O)O—$C_{1-4}$alkyl;

and pharmaceutically acceptable salts, esters and prodrugs thereof.

Illustrative of the invention is a pharmaceutical composition comprising a pharmaceutically acceptable carrier and a compound of Formula (I). Illustrative of the invention is a process for making a pharmaceutical composition comprising mixing a compound of Formula (I) and a pharmaceutically acceptable carrier.

The present invention is further directed to methods for treating or ameliorating a urotensin II-mediated disorder. In particular, the method of the present invention is directed to treating or ameliorating a urotensin II-mediated disorder including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes (for example, Type II diabetes mellitus), and CNS indications including pain, Alzheimer's, convulsions, depression, migraine, psychosis, anxiety, neuromuscular deficit, and stroke.

The present invention is further directed to process for the preparation of the compounds of formula (I), and the pharmaceutical compositions and medicaments thereof.

In another example, the present invention is directed to the use of any of the compounds described herein in the preparation of a medicament for treating: (a) vascular hypertension, (b) heart failure, (c) atherosclerosis, (d) renal failure, (e) nephrotoxicity caused by anti-neoplastic agents, (f) diarrhea caused by anti-neoplastic agents, (g) post-myocardial infarction, (h) pulmonary hypertension, (i) pulmonary fibrosis, (j) diabetes (for example, Type II diabetes mellitus), (k) pain, (l) Alzheimer's, (m) convulsions, (n) depression, (o) migraine, (p) psychosis, (q) anxiety, (r) neuromuscular deficit, or (s) stroke, in a subject in need thereof.

DETAILED DESCRIPTION OF THE INVENTION

The present invention is directed to compounds of formula (I)

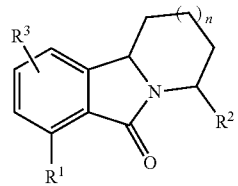

(I)

wherein $R^1$, $R^2$, n and $R^3$ are as herein defined; and pharmaceutically acceptable salts, esters and prodrugs thereof. The compounds of formula (I) are useful as antagonists of the urotensin-II receptor and are therefore useful for the treatment of urotensin-II mediated disorders including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke.

In an embodiment of the present invention, $R^1$ is selected from the group consisting of hydrogen, halogen, cyano, $C_{1-3}$alkyl, $C_{1-3}$alkoxy and $NR^A R^B$; wherein $R^A$ and $R^B$ are each independently selected from the group consisting of hydrogen and $C_{1-4}$alkyl. In another embodiment of the present invention, $R^1$ is selected from the group consisting of hydrogen, halogen, cyano, $C_{1-3}$alkyl and $C_{1-3}$alkoxy. In another embodiment of the present invention, $R^1$ is selected from the group consisting of hydrogen, halogen, $C_{1-3}$alkyl and $C_{1-3}$alkoxy. In another embodiment of the present invention $R^1$ is hydrogen. In another embodiment of the present invention, $R^1$ is $NR^A R^B$; wherein $R^A$ and $R^B$ are each independently selected from the group consisting of hydrogen, methyl, ethyl and t-butyl.

In an embodiment of the present invention, n is an integer from 1 to 3. In another embodiment of the present invention, n is an integer from 0 to 2. In another embodiment of the present invention, n is an integer form 1 to 2.

In an embodiment of the present invention, $R^2$ is selected from the group consisting of phenyl and 5 to 6 membered heteroaryl; wherein the phenyl or 5 to 6 membered heteroaryl is optionally substituted with one to three substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkyl)amino and di($C_{1-4}$alkyl)amino. In another embodiment of the present invention, $R^2$ is selected from the group consisting of phenyl and 5 to 6 membered heteroaryl; wherein the phenyl or 5 to 6 membered heteroaryl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkyl)amino and di($C_{1-4}$alkyl)amino.

In an embodiment of the present invention, $R^2$ is selected from the group consisting of phenyl and 5 to 6 membered heteroaryl. In another embodiment of the present invention $R^2$ is phenyl; wherein the phenyl is optionally substituted with one to three substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkyl)amino and di($C_{1-4}$alkyl)amino. In another embodiment of the present invention $R^2$ is phenyl; wherein the phenyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkyl)amino and di($C_{1-4}$alkyl)amino. In another embodiment of the present invention, $R^2$ is phenyl; wherein the phenyl is optionally substituted with one to two substituents independently selected from $C_{1-4}$alkoxy. In another embodiment of the present invention, $R^2$ is (R)-3,4-dimethoxy-phenyl.

In an embodiment of the present invention, $R^3$ is bound at the three or the four position, and is selected from the group consisting of $NR^C R^D$; wherein $R^C$ and $R^D$ are each independently selected from the group consisting of hydrogen and $C_{1-4}$alkyl. In another embodiment of the present invention, $R^3$ is bound at the three or the four position, and is selected from the group consisting of $NR^C R^D$; wherein $R^C$ and $R^D$ are each independently selected from the group consisting of hydrogen, methyl, ethyl and t-butyl.

In another embodiment of the present invention, $R^3$ is bound at the three or the four position, and is selected from the group consisting of $NR^C R^D$; wherein $R^C$ and $R^D$ are taken together with the nitrogen atom to which they are bound to form a saturated ring structure selected from the group consisting of piperidinyl, piperazinyl and pyrrolidinyl; wherein the saturated ring structure is optionally substituted with one to three substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkyl)amino and di($C_{1-4}$alkyl)amino. In another embodiment of the present invention, $R^3$ is bound at the three or the four position, and is selected from the group consisting of $NR^C R^D$; wherein $R^C$ and $R^D$ are taken together with the nitrogen atom to which they are bound to form a saturated ring structure selected from the group consisting of piperidinyl, piperazinyl and pyrrolidinyl; wherein the saturated ring structure is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkyl)amino and di($C_{1-4}$alkyl)amino.

In another embodiment of the present invention, $R^3$ is bound at the three or the four position, and is selected from the group consisting of $NR^C R^D$; wherein $R^C$ and $R^D$ are taken together with the nitrogen atom to which they are bound to form piperidinyl; wherein the piperidinyl is optionally substituted with one to three substituents independently selected from the group consisting of halogen, hydroxy, $C_{1-4}$alkyl, halogenated $C_{1-4}$alkyl, $C_{1-4}$alkoxy, halogenated $C_{1-4}$alkoxy, cyano, nitro, amino, ($C_{1-4}$alkyl)amino and di($C_{1-4}$alkyl)amino. In another embodiment of the present invention, $R^3$ is bound at the three or the four position, and is selected from the group consisting of $NR^C R^D$; wherein $R^C$ and $R^D$ are taken together with the nitrogen atom to which they are bound to form piperidinyl; wherein the piperidinyl is optionally substituted with one to two substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, nitro, amino, ($C_{1-4}$alkyl)amino and di($C_{1-4}$alkyl)amino.

In another embodiment of the present invention, $R^3$ is bound at the three or four position and is piperazinyl; wherein the piperazinyl is optionally substituted with $C_{1-4}$alkyl. In another embodiment of the present invention, $R^3$ is bound at the three position and is piperazinyl; wherein the piperazinyl is optionally substituted with $C_{1-4}$alkyl. In another embodiment of the present invention, $R^3$ is bound at the three position and is 1-(4-ethyl-piperazinyl).

In an embodiment of the present invention, the compound of formula (I) is selected from the group consisting of 4R-(3,4-dimethoxy-phenyl)-10-(4-ethyl-piperazin-1-yl)-1,3,4,10b-tetrahydro-2H-pyrido[2,1-a] isoindol-6-one; 7R-(3,4-dimethoxy-phenyl)-1-(4-ethyl-piperazin-1-yl)-7,8,9,10,11,11a-hexahydro-azepino[2,1-a]isoindol-5-one; and pharmaceutically acceptable salts, esters and prodrugs thereof.

In an embodiment, the present invention is directed to a mixture of its corresponding stereoisomers, for example a racemic mixture, of the compound of formula (I). In embodiments of the present invention, the compound of formula (I) may be present in a diastereomeric excess of any one of its corresponding four enantiomeric (i.e. the (R,R), (R,S), (S,S) and (S,R) enantiomers), wherein the stereocenters are denoted with the "*" in the structure as shown below

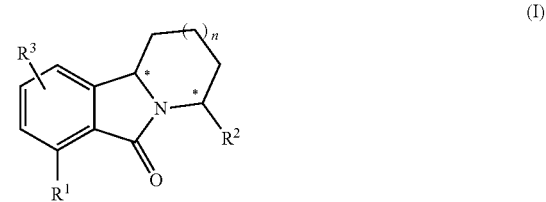

(I)

In an embodiment, the compound of formula (I) is present in an enantiomeric excess of any one its corresponding enantiomeric of greater than or equal to about 75% ee, preferably greater than or equal to about 85% ee, more preferably greater than or equal to about 95% ee, more preferably greater than or equal to about 98% ee, more preferably greater than or equal to about 99% ee.

Additional embodiments of the present invention, include those wherein the substituents selected for one or more of the variables defined herein (i.e. $R^1$, $R^2$, n, and $R^3$) are independently selected to be any individual substituent or any subset of substituents selected from the complete list as defined herein.

In another embodiment of the present invention is any single compound or subset of compounds selected from the representative compounds listed in Table 1, below.

TABLE 1

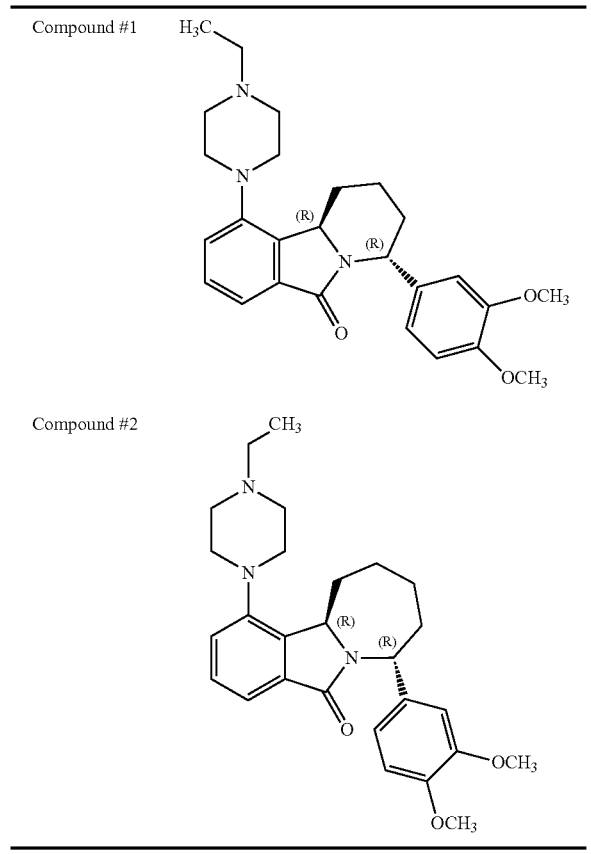

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$" when used with alkyl means a carbon chain composition of 1-4 carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_3$, and the like. Similarly, the term "fluorinated $C_{1-4}$alkyl" shall mean any $C_{1-4}$alkyl group as defined above substituted with at least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{1-4}$" when used with alkoxy means an oxygen ether radical as described above containing 1-4 carbon atoms.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

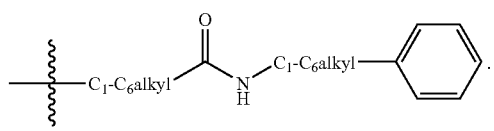

Unless otherwise noted, for the purposes of identifying the carbon atoms on the phenyl portion of the compound of formula (I) to which the $R^3$ substituent group is bound, the carbon atoms on the phenyl portion of the compound of formula (I) shall be numbered as shown in the structure below:

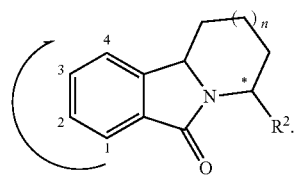

(I)

Abbreviations used in the specification, particularly the Schemes and Examples, are as follows:

| | |
|---|---|
| 9-BBN = | 9-Borabicyclo[3.3.1]nonane |
| CHF = | Chronic Heart Failure |
| CNS = | Central Nervous System |
| DCE = | Dichloroethane |
| DCM = | Dichloromethane |
| DIPEA or DIEA = | Diisopropylethylamine |
| DME = | Dimethyl ether |
| DMF = | Dimethyl formamide |
| DMEM = | Dulbecco's modified Eagle's medium |
| DMSO = | Dimethylsulfoxide |
| EtOAc = | Ethyl acetate |
| HEPES = | 4-(2-Hydroxyethyl)-1-Piperizine Ethane Sulfonic Acid |
| HPLC = | High Pressure Liquid Chromatography |
| IBX = | 2-Iodobenzoic acid |
| Mesyl = | Methylsulfonyl |
| NaOEt = | Sodium Ethoxide |
| NaOt-Bu = | Sodium t-butoxide |
| NMP = | N-methyl-pyrrolidone |
| OTf = | Triflate (i.e. trifluoromethyl-sulfonyl-oxy-) |
| PPh$_3$CH$_3$Br = | Triphenylphosphino bromomethane |
| Sulfolane = | 2,3,4,5-tetrahydrothiophene-1,1-dioxide |
| TEA = | Triethylamine |
| TFA = | Trifluoroacetic Acid |
| THF = | Tetrahydrofuran |

As used herein, unless otherwise noted, the term "isolated form" shall mean that the compound is present in a form which is separate from any solid mixture with another compound(s), solvent system or biological environment. In an embodiment of the present invention, the compound of formula (I) is present as an isolated form.

As used herein, unless otherwise noted, the term "substantially pure compound" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure compound.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula—C(O)O—R wherein R is for example methyl, ethyl, t-butyl, benzyl, phenylethyl, $CH_2$=CH—$CH_2$—, and the like; amides—groups of the formula—C(O)—R' wherein R' is for example methyl, phenyl, trifluoromethyl, and the like; N-sulfonyl derivatives—groups of the formula—$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α-*obs*]/[α-max])×100.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared as outlined in general Scheme 1, below.

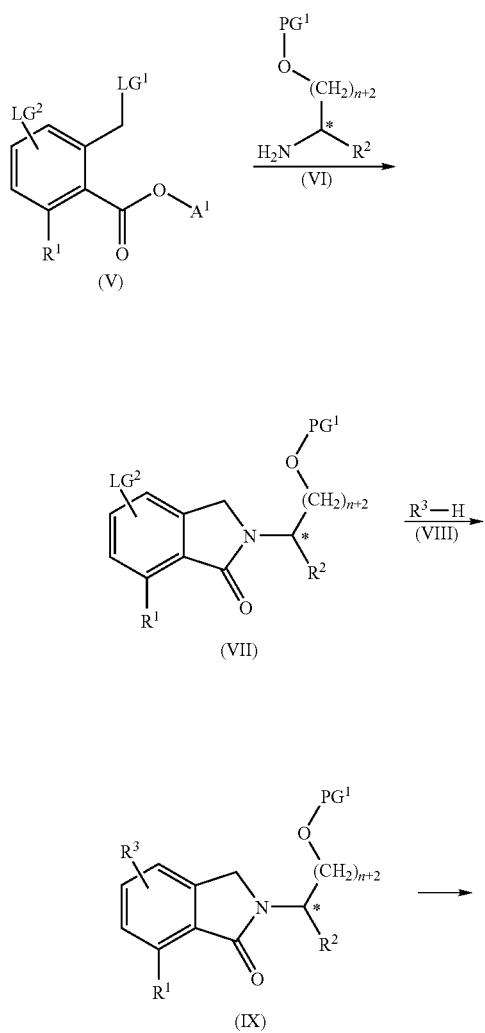

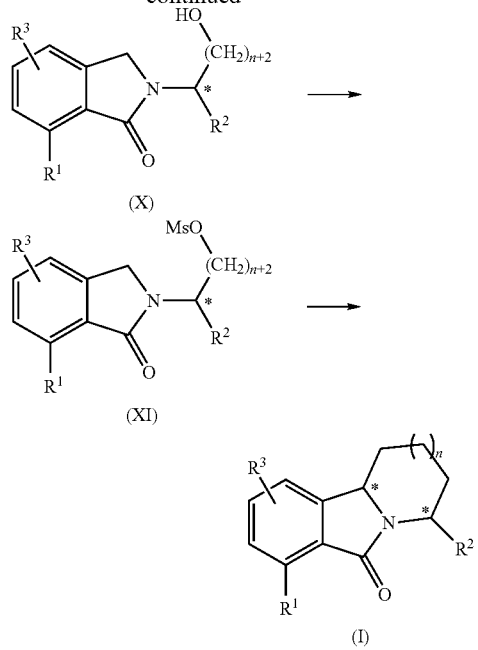

Accordingly, a suitably substituted compound of formula (V), wherein $A^1$ is $C_{1-4}$alkyl, wherein $LG^1$ is a suitably selected leaving groups such as Cl, Br, and the like, preferably $LG^1$ is Br; and wherein $LG^2$ is a suitably selected leaving group such as Br, Cl, I, OTf, and the like, preferably $LG^2$ is Br; a known compound or compound prepared by known methods, is reacted with a suitably substituted compound of formula (VI), wherein $PG^1$ is a suitably selected oxygen protecting group such as benzyl, dimethoxybenzyl, tetrahydropyranyl, and the like, preferably benzyl, preferably other than acetyl; in the presence of an organic base such as TEA, DIPEA, pyridine, and the like; in an organic solvent such as toluene, ethyl acetate, and the like; preferably at a temperature in the range of from about 40° C. to about 110° C., more preferably at about 90° C.; to yield the corresponding compound of formula (VII).

The compound of formula (VII) is reacted with a suitably substituted compound of formula (VIII), a known compound or compound prepared by known methods, in the presence of a suitably selected catalyst such as bis(tert-butylphosphine) palladium (0), and the like; in the presence of a suitably selected phase transfer agent such as cetyl trimethylammonium bromide, butyl-triethylammonium chloride, and the like; in the presence of a suitably selected inorganic base such as potassium hydroxide, sodium hydroxide, potassium carbonate, sodium carbonate, and the like; in an organic solvent such as toluene, benzene, and the like; preferably at a temperature in the range of from about 75° C. to about 100° C., more preferably at about 90° C.; to yield the corresponding compound of formula (IX).

The compound of formula (IX) is de-protected according to known methods; to yield the corresponding compound of formula (X). For example, wherein $PG^1$ is benzyl, the compound of formula (IX) is de-protected by reacting with hydrogen gas, in the presence of a catalyst such as Pd/C, in the presence of a catalytic amount of an acid such as HCl, in a solvent such as ethanol.

The compound of formula (X) is reacted with methanesulfonyl chloride (also known as mesyl chloride), a known compound; in the presence of an organic base such as TEA, DIPEA, pyridine, and the like; in an organic solvent such as DCM, DCE, chloroform, and the like; preferably at a temperature in the range of from about 0° C. to about 25° C., more preferably at about 0° C.; to yield the corresponding compound of formula (XI).

The compound of formula (XI) is reacted with a suitably selected base such as NaOt-Bu, NaOEt, NaH, and the like, preferably NaOt-Bu; in an organic solvent such as DME, THF, acetonitrile, and the like; preferably at a temperature in the range of from about 40° C. to about 80° C., more preferably at about 60° C.; to yield the corresponding compound of formula (I).

One skilled in the art will recognize that if the compound of formula (VI) is present in an enantiomeric excess of one of its corresponding enantiomers (with the stereocenter as denoted by the *, then the compound of formula (I) will be prepared in an enantiomeric excess of the corresponding enantiomer.

One skilled in the art will further recognize that the compound of formula (I) may be further, optionally reacted with an inorganic base such as sodium carbonate, potassium, carbonate, and the like; in an aprotic solvent such as DMF NMP, sulfolane and the like; to yield the corresponding compound of formula (I) wherein the stereo-configuration of the compound is isomerized Compounds of formula (I) wherein n is 2 may alternatively be prepared according to the process as outlined in Scheme 2 below.

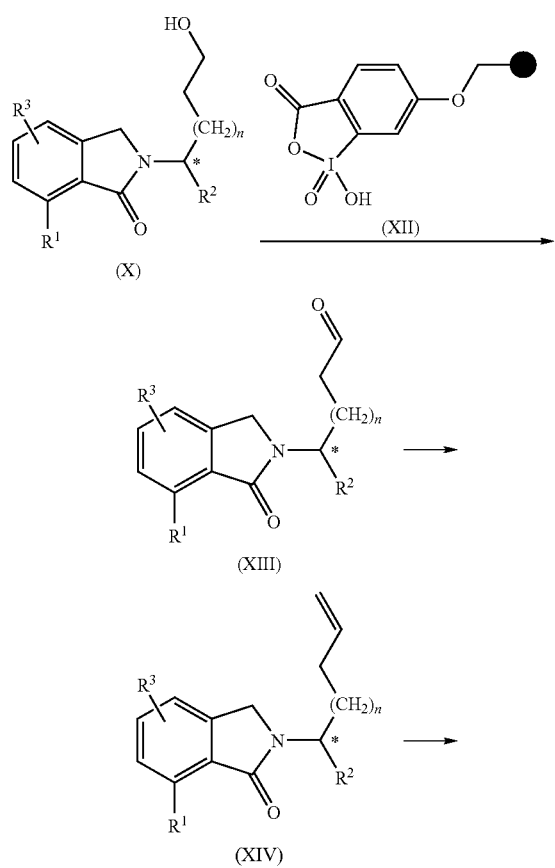

Accordingly, a suitably substituted compound of formula (X), a known compound or compound prepared by known methods, is reacted with a suitably substituted, polymer bound compound of formula (XII), wherein the polymer is denoted by the ● symbol in the compound of formula (XII) above, for example IBX-polystyrene; in an organic solvent such as DCM, DCE, and the like; to yield the corresponding compound of formula (XIII). One skilled in the art will recognize that alternatively, the compound of formula (X) may be reacted via Swern oxidation or via Dess-Martin reaction, according to known methods, to yield the corresponding compound of formula (XIII).

The compound of formula (XII) is reacted with PPh$_3$CH$_3$Br; and the like; in the presence of an inorganic base such as potassium carbonate, sodium carbonate, and the like; in the presence of a suitably selected crown ether such as 18-crown-6,15-crown-5, and the like; in an organic solvent such as DCM, DCE, THF, and the like; to yield the corresponding compound of formula (XIV).

The compound of formula (XIV) is reacted with 9-BBN, and the like; in the presence of in an organic solvent which is inert to borane such as THF, DME, DCE and the like, and the like; preferably at a temperature in the range of from about 0° C. to about 20° C.; followed by work-up with a suitably selected base such as NaOH, and the like; and hydrogen peroxide; to yield the corresponding compound of formula (XV).

The compound of formula (XV) is reacted with mesyl chloride; in the presence of an organic base such as TEA, DIPEA, pyridine, and the like; in an organic solvent such as DCM, DCE, THF, and the like; to yield the corresponding compound of formula (XIa).

The compound of formula (XIa) with a suitably selected base such as sodium t-butoxide, potassium t-butoxide, and the like; in an organic solvent such as DME, and the like; to yield the corresponding compound of formula (Ia).

The present invention is directed to a method for treating a urotensin-II mediated disorder in a patient in need thereof comprising administering to the patient an effective amount of a compound of Formula (I).

An embodiment of the present invention is a method for treating a disorder including, but not limited to, vascular hypertension, heart failure, atherosclerosis, renal failure, nephrotoxicity and diarrhea caused by anti-neoplastic agents, post-myocardial infarction, pulmonary hypertension/fibrosis, diabetes, and CNS indications including pain, Alzheimer's, convulsions, depression, migraine, psychosis, anxiety, neuromuscular deficit, and stroke. Another embodiment of the present invention is a method for treating a urotensin II-mediated disorder selected from the group consisting of heart failure and renal failure.

The present invention also includes the use of an instant compound in the manufacture of a medicament for treating a urotensin II-mediated disorder. The present invention further includes the use of a compound of Formula (I) as a medicine.

The present method of using urotensin II receptor antagonists to reduce anti-neoplastic agent induced diarrhea and nephrotoxicity is applicable in any situations when anti-neoplastic agents (such as cisplatin, cis-diaminedichloroplatinum) are being administered to treat cancers or tumors. However, most often U-II antagonists are used when tumors or cancers being treated are those of solid malignancies, notably those of the bladder, cervix, lung, ovary, and testis such as testicular tumor; bladder cancer; ureterpyelonephritic tumor; prostatic cancer; ovarian cancer; head and neck cancer; non-small-cell lung cancer; esophageal cancer; cervical cancer; neuroblastoma; gastric cancer; small cell lung cancer; bone cancer; non-Hodgkin's lymphomas; tumors of brain, endometrium, upper gastrointestinal tract, head and neck, and thymus; neuroblastoma; and sarcoma of bone and soft tissue. Recent data (American Heart Association Scientific Sessions 2005, "SB-611812 in the treatment of heart failure", by Nicolas Bousette at Montreal General Hospital, Canada) has demonstrated that urotensin II receptor antagonists may be useful for improving cardiac function and for cardiac remodeling associated with chronic heart failure (CHF).

As used herein, the term "neoplasm" refers to an abnormal growth of cells or tissue and is understood to include benign, i.e., non-cancerous growths, and malignant, i.e., cancerous growths. The term "neoplastic" means of or related to neoplasm.

As used herein, the term "agent" is understood to mean a substance that produces a desired effect in a tissue, system, animal, mammal (in particular human), or other subject. Accordingly, the term "anti-neoplastic agent" is understood to mean a substance producing an anti-neoplastic effect in a tissue, system, animal, mammal (in particular human), or other subject. It is understood that an "agent" may be a single compound or a combination or composition of two or more compounds.

Some of the typical anti-neoplastic agents include alkylating agents such as melphalan, chlorambucil, cyclophosphamide, mechlorethamine, hexamethylmelamine, busulfan, carmustine, lomustine, and dacarbazine; antimetabolites such as 5-fluorouracil, methotrexate, cytarabine, mercaptopurine, and thioguanine; antimitotic agents such as paclitaxel, docetaxel, vinblastine, vincristine; topoisomerase I inhibitors such as irinotecan, camptothecin and camptothecin derivatives, for example topotecan; topoisomerase II inhibitors such as doxorubicin; and platinum coordination complexes such as cisplatin and carboplatin.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg or any range therein, and may be given at a dosage of from about 0.01-300 mg/kg/day, or any range therein, preferably from about 0.5-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by the urotensin-II receptor as described herein is required.

The daily dosage of the products may be varied over a wide range from 0.1 to 10,000 mg per adult human per day, or any range therein. For oral administration, the compositions are preferably provided in the form of tablets containing, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 1000 mg/kg of body weight per day, or any range therein. Preferably, the range is from about 0.5 to about 50.0 mg/kg of body weight per day, or any range therein. More preferably, from about 1.0 to about 5.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

(R,R)-4-(3,4-Dimethoxy-phenyl)-10-(4-ethyl-piperazin-1-yl)-1,3,4,10b-tetrahydro-2H-pyrido[2,1-a]isoindol-6-one

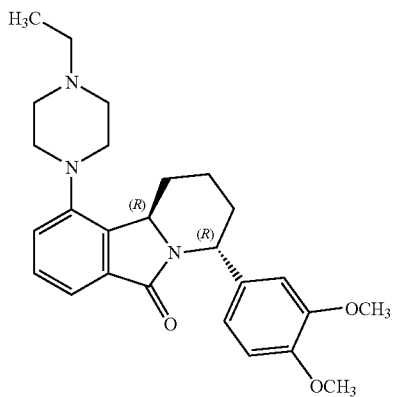 [SMILES: CCN1CCN(c2cccc3c2[C@H]2CCC[C@H](c4ccc(OC)c(OC)c4)N2C3=O)CC1]

Methanesulfonic acid 4-(3,4-dimethoxy-phenyl)-4-[4-(4-ethyl-piperazin-1-yl)-1-oxo-1,3-dihydro-isoindol-2-yl]-butyl ester (112 mg, 0.211 mmol) was dissolved in DME (0.80 mL), and a 4 M solution of NaOtBu in THF (0.5 mL) was added. The resulting mixture was stirred at 60° C. for 1 hour and then allowed to cool to room temperature. The resulting mixture was then poured into water (10 mL) and extracted with EtOAc (2 times, 15 mL). The organic layers were combined, washed with brine (10 mL), dried over $Na_2SO_4$, and concentrated in vacuum to yield a residue. The residue was purified using prep-HPLC 5-90 gradient water (0.2% TFA buffer)/acetonitrile (0.15% TFA buffer) to yield the title compound as a pale yellow solid.

MS$^+$ H 436.40 (100), 437.42 (40)

$^1$H NMR (500 MHz, CDCl$_3$) δ ppm 1.15 (d, J=12.5 Hz, 1H), 1.40 (t, J=7.32 Hz, 3H), 1.79-1.88 (m, 2H), 2.54 (dd, J=23.80, 2.75 Hz, 1H), 2.52 (d, J=18.31 Hz, 1H), 2.89 (t, J=12.05 Hz, 1H), 3.17 (dd, J=7.32, 1.53 Hz, 2H), 3.23 (d, J=12.51 Hz, 1H), 3.29 (d, J=6.41 Hz, 2H), 3.57 (t, J=11.29 Hz, 1H), 3.68 (d, J=10.99 Hz, 1H), 3.76 (d, J=11.29 Hz, 1H), 3.85 (d, J=20.75 Hz, 6H), 4.34 (dd, J=12.05, 3.81 Hz, 1H), 5.78 (d, J=2.75 Hz, 1H), 6.79-6.85 (m, 2H), 7.29 (d, J=7.63 Hz, 1H), 7.50 (t, J=7.78 Hz, 1H), 7.74 (d, J=7.32 Hz, 1H)

$^{13}$C NMR (500 MHz, CDCl$_3$) δ ppm 166.8, 149.4, 148.2, 146.1, 139.1, 133.7, 131.9, 129.9, 123.0, 120.6, 118.8, 111.2, 110.6, 56.1, 555.9, 55.6, 52.2, 51.8, 51.6, 49.4, 49.3, 48.0, 30.4, 27.5, 19.8, 9.10.

Example 2

(R,R)-7-(3,4-Dimethoxy-phenyl)-1-(4-ethyl-piperazin-1-yl)-7,8,9,10,11,11a-hexahydro-azepino[2,1-a]isoindol-5-one

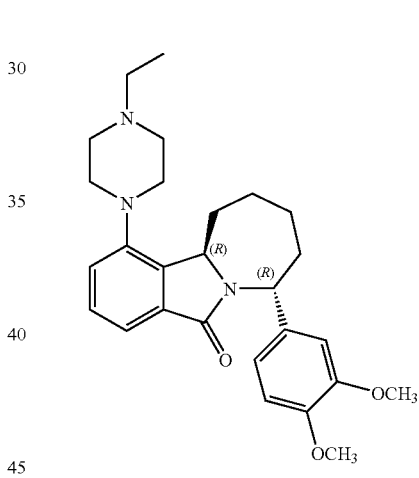

Step A:

(R,R)-2-[1-(3,4-Dimethoxy-phenyl)-4-hydroxy-butyl]-4-(4-ethyl-piperazin-1-yl)-2,3-dihydro-isoindol-1-one (1.2 g, 2.646 mmol) was dissolved in DCM (75 mL), IBX-polystyrene (4.81 g, 5.29 mmol) was added and the resulting mixture was agitated overnight. The reaction mixture was then filtered and washed with DCM. The combined filtrate and washings were concentrated and dried in vacuo to yield 4-(R)-(3,4-dimethoxy-phenyl)-4-[4-(4-ethyl-piperazin-1-yl)-1-oxo-1,3-dihydro-isoindol-2-yl]-butyraldehyde as a yellow fluffy solid.

(M+H)$^+$ 452.0; $^1$H NMR (300 MHz, Chloroform-d) δ ppm 1.14 (t, J=7.16 Hz, 3H) 1.85 (dt, J=6.88, 3.16 Hz, 2H) 2.27 (s, 1H) 2.35-2.72 (m, 7H) 2.96-3.17 (m, 4H) 3.67-3.80 (m, 1H) 3.81-3.95 (m, 1H) superimposed on 3.85 (s, 3H) and 3.88 (s, 3H), 4.22 (d, J=16.95 Hz, 1H) 5.55 (dd, J=9.04, 6.40 Hz, 1H) 6.79-6.92 (m, 2H) 6.92-7.00 (m, 1H) 7.09 (d, J=6.78 Hz, 1H) 7.41 (t, J=7.54 Hz, 1H) 7.47-7.56 (m, 1H) 9.79 (s, 1H).

Step B:

To a suspension of CH$_3$PPh$_3$Br (0.237 g, 0.66 mmol) in DCM (1 mL) was added K$_2$CO$_3$ (0.092 g, 0.66 mmol) and 18-crown-6 (0.004 g). The resulting mixture was stirred for 30 minutes and then a solution of 4-(R)-(3,4-dimethoxy-phenyl)-4-[4-(4-ethyl-piperazin-1-yl)-1-oxo-1,3-dihydro-isoindol-2-yl]-butyraldehyde (0.11 g, 0.33 mmol) in DCM (1 mL) was added dropwise and the resulting mixture refluxed for 4 hours. The resulting mixture was then cooled, filtered through CELITE®, and washed with diethyl ether. The filtrate and washings were concentrated and purified by RPHPLC 10-90 gradient (0.2% TFA buffer)/acetonitrile (0.15% TFA buffer), then washed with saturated $NaHCO_3$ aq. solution (3×15 mL) to yield 2-(R)-[1-(3,4-dimethoxy-phenyl)-pent-4-enyl]-4-(4-ethyl-piperazin-1-yl)-2,3-dihydro-isoindol-1-one as a yellow glassy solid.

$(M+H)^+$ 450.0; $^1H$ NMR (300 MHz, Chloroform-d) δ ppm 1.14 (t, J=7.19 Hz, 3H) 1.93-2.75 (m, 4H) 2.49 (br s, 2H) 2.95-3.71 (m, 8H) 3.75-3.91 (m, 1H) superimposed on 3.79 (s, 3H) and 3.85 (s, 3H), 4.05-4.15 (m, 1H) 4.92-5.00 (m, 2H) 5.50 (t, J=7.09 Hz, 1H) 5.75-5.86 (m, 1H) 6.79-6.92 (m, 2H) 6.92-7.00 (m, 1H) 7.09 (d, J=6.78 Hz, 1H) 7.41 (t, J=7.54 Hz, 1H) 7.47-7.56 (m, 1H) 9.79 (s, 1H).

Step C:

To a solution of 2-(R)-[1-(3,4-Dimethoxy-phenyl)-pent-4-enyl]-4-(4-ethyl-piperazin-1-yl)-2,3-dihydro-isoindol-1-one (0.1 g, 0.22 mmol) in dry THF (3 mL) at 0° C. under nitrogen was slowly added a THF solution (0.5 M) of 9-BBN, while maintaining the temperature below about 3° C. The resulting mixture was stirred at 0° C. for 3 hours and then at 20° C. for 18 hours. After the mixture was cooled to 0° C., water was added (0.12 mL). When effervescence had subsided, aq. NaOH (3M, 0.27 mL) followed by 30% aq. $H_2O_2$ (0.32 mL), while maintaining the temperature below 50° C. After the addition, the resulting mixture was heated at 50° C. for 3.5 hours, cooled and saturated with solid potassium carbonate. The resulting mixture was filtered, and the filtrate was extracted with EtOAc (2×10 mL). The combined extracts were washed with brine, dried over anhydrous $Na_2SO_4$ and concentrated. The resulting residue was purified by RPHPLC 10-60 gradient (0.2% TFA buffer)/acetonitrile (0.15% TFA buffer), then washed with saturated $NaHCO_3$ aq. solution (3×15 mL) to yield 2-[1-(R)-(3,4-Dimethoxy-phenyl)-5-hydroxy-pentyl]-4-(4-ethyl-piperazin-1-yl)-2,3-dihydro-isoindol-1-one as a free amine.

$(M+H)^+$ 468.0; $^1H$ NMR (400 MHz, Chloroform-d) δ ppm 1.13 (t, J=7.21 Hz, 3H) 1.65 (m, 2H) 1.82-2.15 (m, 2H) 2.06-2.16 (m, 2H) 2.48 (q, J=7.25 Hz, 2H) 2.59 (br. s, 2H) 3.00-3.12 (m, 2H) 3.50 (br s, 2H), 3.65 (d, J=4.65 Hz, 4H) 3.77-3.93 (m, 1H) superimposed on 3.85 (s, 3H) and 3.93 (s, 3H) 4.22 (d, J=16.87 Hz, 2H) 5.56 (dd, J=9.29, 6.36 Hz, 1H) 6.84 (d, J=8.31 Hz, 1H) 6.90 (d, J=1.96 Hz, 1H) 6.92-6.98 (m, 1H) 7.08 (d, J=8.07 Hz, 1H) 7.40 (t, J=7.83 Hz, 1H) 7.50-7.54 (m, 1H).

Step D:

2-[1-(R)-(3,4-Dimethoxy-phenyl)-5-hydroxy-pentyl]-4-(4-ethyl-piperazin-1-yl)-2,3-dihydro-isoindol-1-one (0.05 g, 0.11 mmol) was dissolved in DCM (3 mL) and triethylamine (45.4 µL, 0.16 mmol) was added and the resulting mixture was cooled to 0° C. Methanesulfonyl chloride was then added dropwise and the resulting mixture was stirred at this temperature for 2 hours. The resulting solution was concentrated and the residue was purified by RPHPLC 10-85 gradient (0.2% TFA buffer)/acetonitrile (0.15% TFA buffer), then washed with saturated $NaHCO_3$ aq. solution (3×15 mL) to yield 5-(R)-(3,4-dimethoxy-phenyl)-5-[4-(4-ethyl-piperazin-1-yl)-1-oxo-1,3-dihydro-isoindol-2-yl]-pentyl ester methanesulfonic acid as a clear glassy semi-solid.

$(M+H)^+$ 546.2; $^1H$ NMR (400 MHz, Chloroform-d) δ ppm 1.17 (t, J=7.16 Hz, 3H) 1.47-1.58 (m, 2H) 1.78-1.97 (m, 2H) 2.07-2.20 (m, 2H) 2.46-2.71 (br. m, 5H) 2.97 (s, 3H) 3.09 (br m, 3H) 3.29-3.69 (br. s, 3H) 3.85 (s, 3H) 3.88 (s, 3H) 3.92 (d, J=17.12 Hz, 1H) 4.19-4.28 (m, 2H) 5.55 (dd, J=9.3, 6.6 Hz, 1H) 6.85 (d, J=8.31 Hz, 1H) 6.89 (d, J=1.71 Hz, 1H) 6.91-6.98 (m, 1H) 7.10 (d, J=7.83 Hz, 1H) 7.41 (t, J=7.70 Hz, 1H) 7.48-7.56 (m, 1H).

Step E:

5-(R)-(3,4-dimethoxy-phenyl)-5-[4-(4-ethyl-piperazin-1-yl)-1-oxo-1,3-dihydro-isoindol-2-yl]-pentyl ester methanesulfonic acid (0.03 g, 0.055 mmol) was dissolved in DME (0.5 mL) and sodium t-butoxide (31.7 mg, 0.33 mmol) was added and the resulting mixture heated at 65° C. overnight. The resulting mixture was then cooled to room temperature, filtered and washed with DCM. The combined filtrate and washings were concentrated. The resulting residue was purified by RPHPLC 10-80 gradient (0.2% TFA buffer)/acetonitrile (0.15% TFA buffer) to yield the title compound, as its corresponding TFA salt, as a white solid.

$(M+H)^+$ 450.43; $^1H$ NMR (400 MHz, Chloroform-d) δ ppm 0.91 (t, J=6.89 Hz, 3H) 1.22-1.31 (m, 2H) 1.33-1.45 (m, 2H) 1.61-1.78 (m, 2H) 2.02-2.15 (m, 2H) 2.33-2.51 (br. s, 4H), 2.87-3.01 (br m, 2H) 3.16-3.52 (m, 4H) 3.85 (s, 3H) 3.88 (s, 3H) 4.19-4.28 (d, J=17.02 Hz, 1H) 5.55 (t, J=6.5 Hz, 1H) 6.75 (d, J=8.02 Hz, 1H) 6.83 (d, J=1.71 Hz, 1H) 6.91-6.98 (m, 1H) 7.15 (d, J=7.80 Hz, 1H) 7.41 (t, J=7.70 Hz, 1H) 7.48-7.56 (m, 1H).

Example 3

Rat UII Calcium Mobilization FLIPR Assay

A calcium mobilization assay based on a Fluorescence Imaging Plate

Reader (FLIPR, Molecular Devices, Sunnyvale, Calif.) was used to determine antagonist activity, after a 5 min incubation, in response to the agonist cyclic peptide (Ac)-CFWK (2-NaI)C—$NH_2$ (FLIPR $EC_{50}$=0.54±0.2 nM, rU-II Ki=0.12±0.05 nM) at 1 nM (W. A. Kinney, H. R. Almond, Jr., J. Qi, C. E. Smith, R. J. Santulli, L. de Garavilla, P. Andrade-Gordon, D. S. Cho, A. M. Everson, M. A. Feinstein, P. A. Leung, B. E. Maryanoff, *Angew. Chem., Intl. Ed.* 2002, 41, 2940-2944), in CHO cells transfected with rat GPR14 (U-II receptor) (M. Tal, D. A. Ammar, M. Karpuj, V. Krizhanovsky, M. Naim, D. A. Thompson, *Biochem. Biophys. Res. Commun.* 1995, 209, 752-759. A. Marchese, M. Heiber, T. Nguyen, H. Heng, V. R. Saldivia, R. Cheng, P. M. Murphy, L. C. Tsui, X. Shi, P. Gregor, *Genomics* 1995, 29, 335-344.).

To derive these cells, the complete coding sequence of rat U-II (Genbank Accession No. U32673) was amplified by nested PCR from rat heart marathon-Ready cDNA. PCR was carried out by using the DNA polymerase PFU (Stratagene) following conditions suggested by the manufacturer. The PCR products were cloned into pcDNA3 (Invitrogen) digested with EcoR I and Xba I. Clones containing rat U-II receptor were verified by complete sequencing of the U-II receptor insert to ensure a lack of PCR-introduced errors. The constructed vector was transfected into CHO cells by using lipofectamine (GIBCO BRL). CHO cells with high expression of rat U-II receptor were selected and established as stable cell lines by using G418. CHO cells were seeded at 25,000 cells per well into 96-well, black-wall, clear-bottom microtiter plates 24 h before assay. Cells in culture media (DMEM/F12 containing 15 mM HEPES, L-glutamine, pyridoxine hydrochloride; 10% fetal bovine serum; 1 mg/mL G418 sulfate; antibiotic-antimycotic; pH 7.4) were loaded with proprietary dye, from the FLIPR Calcium Assay Kit (Molecular Devices), prepared in assay buffer (Hanks Balanced Salts Solution, 20 mM HEPES, 0.1% BSA, 2.5 mM probenecid, pH 7.4), and incubated for 1 h at 37° C. Calcium mobilization determinations were performed at room temperature (23° C.). The use of rat GPR14 was considered acceptable, because human U-II has similar affinity for human or rat GPR14 in the transfected cells (S. A. Douglas, E. H. Ohlstein, *Trends Cardiovasc. Med.* 2000, 10, 229-237).

Representative compounds of the present invention were assayed according the procedure described above, with results as listed in Table 2 below.

TABLE 2

| Rat UII FLIPR Average Ki (μM) | |
| --- | --- |
| Compound No. | Ki (μM) |
| 1 | 0.006 |
| 2 | 0.034 |

Example 4

Human Radioligand Binding Assay

Human Skeletal Muscle Myoblasts (HSMM) were obtained from Cambrex, and were cultured according to manufacturer's instruction. Cell viability was examined by trypan blue exclusion. Cells at less than 4 passages were used in all studies. For the ($^{125}$I)-U-II binding experiments (Described in: "Characterization of Functional Urotensin II Receptors in Human Skeletal Muscle Myoblasts: Comparison with Angiotensin II Receptors" J. Qi, L. K. Minor, C. Smith, B, Hu, J. Yang, P. Andrade-Gordon, B. Damiano, *Peptides* 2005, 26, 683-690.), HSMM were plated in 12-well Costar plates in complete medium for 48 h to reach 70% confluence. The binding medium used was Dulbecco's modified Eagle's medium (DMEM) containing 2 mg/ml BSA and 25 mM HEPES (pH 7.4). The cells were washed at room temperature 2× with the binding medium, and were incubated with 0.2 ml per well of prepared binding medium containing 0.150 nM ($^{125}$I)-U-II and compounds for 3 h. The cells were washed 4× with the binding medium and solubilized in 1% SDS and 0.5 N NaOH. Radioactivity was quantified by gamma counting.

Radiolabeled ($^{125}$I)-U-II bound specifically and saturably to intact adherent HSMM. The binding assays were performed at 25° C. to lower nonspecific uptake of ($^{125}$I)-U-II by the cells that was seen at 37° C. Using this method, the nonspecific binding was below 10% of total binding. Analysis of the saturation data using the non-linear curve-fitting technique of GraphPad Prism Version 3.0 revealed that the best fit observed was for a one-site model. The derived $K_d$ value was 0.309±0.022 nM (N=3 experiments) with the Hill slope close to unity. Based on the number of cells in a well and Bmax value, the number of UT receptors in HSMM was 2311±236 per cell (N=3 experiments). A time course experiment demonstrated that ($^{125}$I)-U-II binding to HSMM reached steady state at 3 h, and remained constant up to 5 hr, the longest time point measured. Human U-II, when add at time 0, efficiently displaced specific binding of ($^{125}$I)-U-II with a Ki of 0.425±0.096 nM (N=3 experiments).

Representative compounds of the present invention were assayed according the procedure described above, with results as listed in Table 3 below.

TABLE 3

| Human UII Average Binding Ki (μM) | |
| --- | --- |
| Compound No. | Ki (μM) |
| 1 | 0.064 |
| 2 | not tested |

Example 5

Human UII Calcium Mobilization Assay

6D9 human rhabdomyosarcoma cells were seeded into tissue culture treated 384-well black-walled clear bottom plates (3712, Corning Incorporated, Corning, N.Y.) at 8,000 cells/well in 25 μL of culture medium, and maintained in an incubator (5% $CO_2$ at 37° C.) for 22 hrs prior to the calcium mobilization assay. 25 μL of dye solution was added to the wells such that the final liquid volume before agonist/antagonist treatment was 50 μL for all assays. The cell plates were incubated at 37° C. for 45 minutes and the fluorescence intensity was measured on a Fluorometric Imaging Plate Reader (FLIPR$^{TETRA}$, Molecular Devices, Sunnyvale, Calif.).

Antagonist and agonist U-II were added at room temperature on the FLIPR$^{TETRA}$, and the fluorescence intensity before and after addition was measured over a period of 4 minutes. The dye incubation time and temperature as well as instrument setting was adjusted so the fluorescence intensity could be compared between plates on the same day. $EC_{50}$ and $IC_{50}$ were analyzed using GraphPad Prism 4 software (GraphPad Software Inc., San Diego, Calif.).

Materials and reagent Preparation: Human Rhabdomyosarcoma cells (6D9: isolated by dilution subcloning of RMS13 cells, ATCC® Number: CRL-2061, American Type Culture Collection ATCC, Manassas, Va.) was maintained in RPMI-1640 medium (30-2001, ATCC, Manassas, Va.) supplemented with 10% (v/v) Fetal Bovine Serum (SH30071.03, Hyclone, Logan, Utah).

Dye preparation: BD™ Calcium Assay Kit (80500-301, BD Biosciences, Rockville, Md.) was prepared according to the manufacture's instruction in 1× Hanks' balanced salt solution (HBSS, 21-023-CV, Mediatech, Inc. Herndon, Va.) containing 20 mM HEPES buffer (25-060-CI, Mediatech, Inc. Herndon, Va.). Final dye loading conditions included 1.25 mM probenecid (P36400, Invitrogen, Carlsbad, Calif.) and 0.01% FBS.

Agonist and antagonist preparation: Human U-II stock (U-7257, Sigma, St. Louis, Mo.) was prepared in acidified water (pH 4.95) at 5 mM. Urantide (PUT-3639-PI, Peptide International, Louisville, Ky.) was prepared in water at 5 mM. For assays, U-II agonist, U-II antagonist and urantide were diluted with HBSS/HEPES containing 0.01% FBS.

Test compounds were dissolved in DMSO at 10 mM concentration. The serial dilutions were carried out in HBSS/HEPES. The highest final DMSO concentration was at 0.1%.

Representative compounds of the present invention were assayed according the procedure described above, with results as listed in Table 4 below.

TABLE 4

| Human UII $Ca^+$ Mobilization Average $IC_{50}$ (μM) | |
| --- | --- |
| Compound No. | Ki (μM) |
| 1 | 0.34 |
| 2 | not tested |

Example 6

Oral Formulation

Prophetic Example

As a specific embodiment of an oral composition, 100 mg of the compound prepared as in Example 1 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All publications disclosed in the above specification are hereby incorporated by reference in full.

What is claimed is:

1. A compound of formula (I)

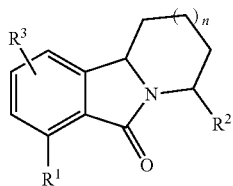

(I)

wherein $R^1$ is selected from the group consisting of hydrogen, halogen, cyano, $C_{1-3}$alkyl, $C_{1-3}$alkoxy and $NR^A R^B$; wherein $R^A$ and $R^B$ are each independently selected from the group consisting of hydrogen and $C_{1-4}$alkyl;

n is an integer from 0 to 3;

$R^2$ is selected from the group consisting of phenyl and 5 to 6 membered heteroaryl; wherein the phenyl or 5 to 6 membered heteroaryl is optionally substituted with one or more substituents independently selected from the group consisting of halogen, hydroxy, $C_{1-4}$-alkyl, halogenated $C_{1-4}$-alkyl, $C_{1-4}$-alkoxy, halogenated $C_{1-4}$-alkoxy, cyano, nitro, amino, ($C_{1-4}$-alkyl)amino, di($C_{1-4}$-alkyl)amino and —C(O)O—$C_{1-4}$-alkyl;

$R^3$ is bound at the three or the four position, and is $NR^C R^D$; wherein $R^C$ and $R^D$ are each independently selected from the group consisting of hydrogen and $C_{1-4}$-alkyl; alternatively, $R^C$ and $R^D$ are taken together with the nitrogen atom to which they are bound to form a saturated ring structure selected from the group consisting of piperidinyl, piperazinyl and pyrrolidinyl;

wherein the saturated ring structure is optionally substituted with one or more substituents independently selected from the group consisting of halogen, hydroxy, $C_{1-4}$-alkyl, halogenated $C_{1-4}$-alkyl, $C_{1-4}$alkoxy, halogenated $C_{1-4}$-alkoxy, cyano, nitro, amino, ($C_{1-4}$-alkyl)amino, di($C_{1-4}$-alkyl)amino and —C(O)O—$C_{1-4}$-alkyl;

or a pharmaceutically acceptable salt or ester thereof.

2. A compound as in claim 1, wherein n is an integer from 0 to 2;

$R^2$ is selected from the group consisting of phenyl and 5 to 6 membered heteroaryl; wherein the phenyl or 5 to 6 membered heteroaryl is optionally substituted with one to three substituents independently selected from the group consisting of halogen, hydroxy, $C_{1-4}$-alkyl, halogenated $C_{1-4}$-alkyl, $C_{1-4}$-alkoxy, halogenated $C_{1-4}$-alkoxy, cyano, nitro, amino, ($C_{1-4}$-alkyl)amino and di($C_{1-4}$-alkyl)amino;

$R^3$ is bound at the three or the four position, and is $NR^C R^D$; wherein $R^C$ and $R^D$ are taken together with the nitrogen atom to which they are bound to form a saturated ring structure selected from the group consisting of piperidinyl, piperazinyl and pyrrolidinyl;

wherein the saturated ring structure is optionally substituted with one to three substituents independently selected from the group consisting of halogen, hydroxy, $C_{1-4}$-alkyl, halogenated $C_{1-4}$-alkyl, $C_{1-4}$alkoxy, halogenated $C_{1-4}$-alkoxy, cyano, nitro, amino, ($C_{1-4}$-alkyl)amino and di($C_{1-4}$-alkyl)amino;

or a pharmaceutically acceptable salt or ester thereof.

3. A compound as in claim 1, wherein $R^1$ is hydrogen;

n is an integer from 1 to 2;

$R^2$ is phenyl; wherein the phenyl is optionally substituted with one to two substituents independently selected from $C_{1-4}$-alkoxy;

$R^3$ is bound at the three position and is piperazinyl; wherein the piperazinyl is optionally substituted with $C_{1-4}$-alkyl;

or a pharmaceutically acceptable salt or ester thereof.

4. A compound as in claim 1, wherein $R^1$ is hydrogen;

n is an integer from 1 to 2;

$R^2$ is (R)-3,4-dimethoxy-phenyl;

$R^3$ is bound at the three position and is 1-(4-ethyl-piperazinyl);

or a pharmaceutically acceptable salt or ester thereof.

5. A compound selected from the group consisting of 4R-(3,4-Dimethoxy-phenyl)-10-(4-ethyl-piperazin-1-yl)-1,3,4,10b-tetrahydro-2H-pyrido[2,1-a]isoindol-6-one;

7R-(3,4-Dimethoxy-phenyl)-1-(4-ethyl-piperazin-1-yl)-7,8,9,10,11,11a-hexahydro-azepino[2,1-a]isoindol-5-one;

and pharmaceutically acceptable salt or ester thereof.

6. A pharmaceutical composition comprising a compound according to claim 1 and a pharmaceutically acceptable carrier.

* * * * *